United States Patent [19]

Bertelli

[11] Patent Number: 4,607,024
[45] Date of Patent: Aug. 19, 1986

[54] EPOXYPROPYLPHOSPHONATE SALT OF JESAMYCIN AND PHARMACEUTICAL COMPOSITION CONTAINING SAME

[75] Inventor: Alberto Bertelli, Milan, Italy

[73] Assignee: Schering S.p.A., Milan, Italy

[21] Appl. No.: 658,493

[22] Filed: Oct. 9, 1984

[30] Foreign Application Priority Data

Oct. 7, 1983 [IT] Italy ................................ 23185 A/83

[51] Int. Cl.$^4$ ...................... A61K 31/71; C07H 17/08
[52] U.S. Cl. ...................................... 514/28; 536/7.1; 536/117
[58] Field of Search .................... 536/7.1, 117; 514/28

[56] References Cited

U.S. PATENT DOCUMENTS 3,959,252  5/1976  Osono et al. ..................... 536/7.1
4,001,399  1/1977  Osono et al. ..................... 536/7.1

OTHER PUBLICATIONS

"The Merck Index", published by Merck & Co., Inc., 1976, p. 4110.

*Primary Examiner*—Johnnie R. Brown
*Attorney, Agent, or Firm*—Bucknam and Archer

[57] ABSTRACT

A new salt of the macrolide antibiotic Josamycin with (−)-cis-1,4-epoxypropionylphosphonic acid, of formula (I)

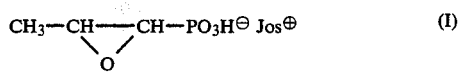

The salt (I), prepared from Josamycin base and phosphomycin, possesses favorable antimicrobial and pharmacokinetics properties.

5 Claims, No Drawings

EPOXYPROPYLPHOSPHONATE SALT OF JESAMYCIN AND PHARMACEUTICAL COMPOSITION CONTAINING SAME

The present invention relates to a new salt of the macrolide antibiotic Josamycin with (−)-cis-1,2-epoxypropyl phosphonic acid, also known as phosphomycin (INN, International Non-proprietary Name).

Josamycin, a known substance widely employed in therapy, was first described in German laid open application No. 1, 492, 035. Its pharmacological properties are summarized in Drugs of Today, 13, 8, 1977. Also phosphomycin has been employed as an antibacterial agent for a long time: it may be prepared either by a synthetic route (Belgian Pat. Nos. 723,072 and 723,073) or by fermentation of a *Streptomyces fradiae* strain (Belgian Pat. No. 718,507).

It has now been found that the salt of Josamycin with phosphomycin, of the following formula (I)

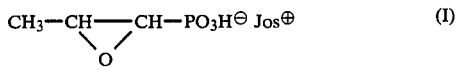

wherein, for brevity purposes, the structural formula of Josamycin has been replaced by the symbol Jos, is endowed with surprisingly favourable pharmacokinetics characteristics. More particularly, the salt of formula (I) is highly absorbed when administered by oral route and causes significantly long lasting tissue and haematic levels which are nearly twice those obtained upon administration of equivalent amounts of Josamycin, both as the free base and in the form of the corresponding propionate. In addition, the product displays a high solubility in water and, accordingly, may be administered also by parenteral route. Finally, the compound which is the object of the present invention is very little toxic, whereas its antibacterial spectrum is comparable with that of Josamycin: thus, it can advantageously be employed in the treatment of infections caused by Josamycin-sensitive bacteria.

Accordingly, a further object of the present invention are the pharmaceutical compositions containing, as the active ingredient, the salt of formula I in admixture with the commonly acceptable pharmaceutical carriers. For instance, the compound of the invention may be incorporated into tablets, capsules or granules for oral administration, suppositories for rectal administration, ointments for topical use or solutions, when the parenteral route is preferred. The above pharmaceutical formulations may contain from about 10 to about 1500 mg of active ingredient.

Representative, though not limitative examples of the pharmaceutical formulations according to the invention are: capsules, tablets, sugar coated tablets containing 125–500–1000 mg of active ingredient; suppositories, containing 0.25–0.5–1 or 2 g of active ingredient; ointments, creams or lotions containing from 10 to 25% by weight of active product; vials for parenteral use, containing from 500 to 2000 mg of active compound. The daily dosage at which the compound of the invention must effectively be administered depend on the actual therapeutical needs and, in general, from 1 to 2 capsules, tablets or sugar coated tablets 3 or 4 times per day; from 1 to 3 suppositories; from 3 to 6 tea-spoons of granulated preparations; from 1 to 2 or more 2–5 or 10 ml vials, by intramuscular, intravenous or slow-perfusion route, two or more times per day.

The compound of the invention is conveniently prepared from Josamycin base and phosphomycin acid, in turn obtained from sodium phosphomycin upon treatment with ion exchange resins, in an acetone medium.

The following Example illustrates the method of preparation according to the invention, without representing a limitation of the invention itself.

EXAMPLE

A. 1.1 Grams (0.006 moles) of disodium phosphomycin were dissolved in 50 ml of methanol to, the solution was added 10 g of Amberlite ®200 and the mixture was stirred for about 10 minutes. After filtering, the filtrate was evaporated off under reduced pressure. Whereby phosphomycin was obtained as an oily residue.

B.
The oil residue obtained under (A) was dissolved in 10 ml of acetone and to the resulting solution was added a solution of 5.0 g (0.006 moles) of Josamycin base in 50 ml of acetone. After stirring for 10 minutes, the solvent was evaporated off under reduced pressure. A crystalline residue was obtained, which was washed with anhydrous diethyl ether. After filtering, 6 g of a white crystalline product, melting at 149°–158° C. was obtained.

I.R. characteristic absorption bands (in nujol mull): 3450, 1730, 1600, 1510, 1460, expressed in $cm^{-1}$.

N.M.R. characteristic resonance peaks (in DMSO-$d_6$ at 60 MHz, with TMS as the internal standard: 0.99 (m); 2.01 (s); 2.4 (s); 3.4 (s); 4.15 (s); 5 (s); 9.6 (s), expressed as $\delta$ (ppm).

s=singlet; m=multiplet.

The so obtained product was investigated with respect to acute and chronic toxicity, as well as teratological, pharmacokinetics and antibacterial activity.

TOXICOLOGICAL TESTS

Acute toxicity

The acute toxicity of the compound of the invention was determined on mice and rats (Swiss mice of both sexes and Wistar rats of both sexes), after oral and intravenous administration of the compound of the invention. It was expressed as an $LD_{50}$ value, calculated according to the method of Lichtfield and Wilcoxon. The obtained intravenous values were 418 mg/kg in rats and 386 mg/kg in mice. The oral $LD_{50}$ could not be determined, as no deaths were observed with administrations of the compound of the invention up to 5000 mg/kg.

Chronic toxicity

Three groups of male Wistar rats (average weight: 155 g) were used in this experiment. A first group received a daily dosage of 250 mg/kg of the compound to be tested by oral route, a second group received a daily amount of 50 mg/kg of the same substance by subcutaneous route, a third group (controls) received nothing. The experiment was carried on for 3 consecutive months.

Since the beginning, as well as during and after the treatment, the animals were constantly monitored with respect to the increase in body weight, the haematic crasis, the urinary elimination and various biochemical parameters. At the end of the treatment, all the animals were sacrificed and subjected to anatomo-pathological investigations. The obtained results did not reveal any alteration of toxic character ascribable to the administration of the tested substance.

Teratological and neonatal investigations

The administration of the compound of the invention to pregnant rats (50 mg/kg s.c. or 300 mg/kg p.o. daily, from the first to the 15th day of pregnancy) or to pregnant rabbits (50 mg/kg s.c. or 300 mg/kg p.o. daily, from the 7th to the 15th day of pregnancy) under the employed experimental conditions, did not cause any alteration of the normal embrional or fetal development.

Also the growth and the survival of the newborns after 30 days from the birth were comparable with those of the controls.

Absorption tests and haematic levels

The new Josamycin salt according to the invention induces haematic levels of Josamycin twice those obtained upon administration of equivalent dosages of the same substance, both as the free base and in the form of the corresponding propionate.

In representative experiments carried out on New Zealand rabbits, it was found that, after oral administration of the new Josamycin salt of formula I at dosages corresponding to 20 and 75 mg/kg of Josamycin, higher haematic levels of the substance were obtained, under the same experimental conditions (0.794 μg/ml for the compound of the invention and 0.407 μg/ml for Josamycin).

In addition, the haematic levels induced by the new salt of formula I are also longer lasting, as it can be inferred from a determination carried out at the 6th hour since the administration (0.297 μg/ml for the new Josamycin salt and 0.139 μg/ml for Josamycin as such).

The determination of the Josamycin levels was performed both by biological way (Grove, D. C., and Randall, W. A., 1955) and by High Pressure Liquid Chromatography (HPLC).

Microbiological tests

In vitro tests, carried out by the agar dilution method, and in vivo experiments on the infected mice have confirmed that the antibacterial spectrum of the new salt of formula I is comparable with that of Josamycin.

I claim:

1. (−)-cis-1,2-Epoxypropylphosphonate of Josamycin of formula (I)

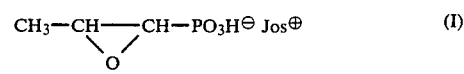

wherein the symbol Jos stands for Josamycin.

2. A pharmaceutical composition with antibacterial activity containing, as the active ingredient, an effective amount of the compound defined in claim 1 and a pharmaceutically acceptable carrier.

3. A pharmaceutical composition as defined in claim 2 in dosage form suitable for the administration of from 10 mg/day to 10 g/day of said active ingredient.

4. A pharmaceutical composition as defined in claim 3 to be administered by oral, rectal, topical or parenteral route in the form of tablets, capsules, granules, suppositories, ointments or vials.

5. The process of preparation of the compound (−)-cis-1,2-Epoxypropylphosphonate of Josamycin of formula (I)

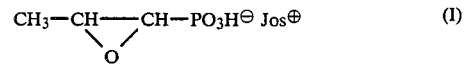

wherein the symbol Jos stands for Josamycin which consists of reacting sodium phosphomycin with an ion exchange resin in the acid form to obtain phosphomycin acid as an oil, reacting said oil in acetone with josamycin in acetone to obtain a crystalline residue and isolating said salt therefrom.

* * * * *